United States Patent [19]

Kulmala et al.

[11] Patent Number: 5,618,985

[45] Date of Patent: Apr. 8, 1997

[54] PROCESS FOR THE PREPARATION OF 2-N-BUTYL-2-ETHYL-1,3-PROPANE DIOL

[75] Inventors: Kari Kulmala, Porvoo, Finland; Kjell Ankner, Mölnlycke, Sweden; Lea Rintala, Porvoo, Finland

[73] Assignee: Neste Oy, Espoo, Finland

[21] Appl. No.: 381,919

[22] PCT Filed: Jun. 20, 1994

[86] PCT No.: PCT/FI94/00273

§ 371 Date: May 4, 1995

§ 102(e) Date: May 4, 1995

[87] PCT Pub. No.: WO95/00464

PCT Pub. Date: Jan. 5, 1995

[30] Foreign Application Priority Data

Jun. 28, 1993 [FI] Finland .................... 932968

[51] Int. Cl.$^6$ .................................... C07C 27/00
[52] U.S. Cl. ........................................... 568/853
[58] Field of Search ............................... 568/853

[56] References Cited

U.S. PATENT DOCUMENTS

| | | | |
|---|---|---|---|
| 2,240,734 | 5/1941 | Wyler et al. | 568/853 |
| 2,413,803 | 1/1947 | Tribit . | |
| 2,501,865 | 3/1950 | Fuchs et al. | 568/853 |
| 2,534,191 | 12/1950 | Cryer et al. | 568/853 |
| 4,215,076 | 7/1980 | Stueben et al. . | |
| 4,514,578 | 4/1985 | Immel et al. | 568/853 |
| 5,146,004 | 9/1992 | Morris et al. . | |

FOREIGN PATENT DOCUMENTS

| | | | |
|---|---|---|---|
| 640927 | 5/1962 | Canada | 568/853 |
| 0367743 | 5/1990 | European Pat. Off. . | |
| 62-129233 | 6/1987 | Japan . | |
| 1-299240 | 12/1989 | Japan . | |
| 2-040333 | 2/1990 | Japan . | |
| 2-62836 | 3/1990 | Japan . | |

*Primary Examiner*—Rebecca Cook
*Attorney, Agent, or Firm*—Birch, Stewart, Kolasch & Birch, LLP

[57] ABSTRACT

The invention relates to a novel, technically simple but efficient and high-yield process for the preparation of 2-n-butyl-2-ethyl-1,3-propane diol from 2-ethyl hexanal and formaldehyde by using a basic alkali metal hydroxide or earth alkali metal hydroxide catalyst. In the process according to the invention, cationic or neutral phase transfer catalysts are additionally used for promoting the reaction. The correct choice of the sources of the initial material components is also essential. 2-n-butyl-2-ethyl-1,3-propane diol is used, for example, in the paint industry in the preparation of pulverous paints.

2 Claims, No Drawings

PROCESS FOR THE PREPARATION OF 2-N-BUTYL-2-ETHYL-1,3-PROPANE DIOL

This is a continuation of PCT/FI 94/00273.

The object of the invention is a new, technically simple but efficient process for the preparation of 2-n-butyl-2-ethyl-1,3-propane diol from 2-ethyl hexanal and formaldehyde. The invention is based on correctly selected sources of the initial components and on the use of correctly selected catalysts.

2-n-butyl-2-ethyl-1,3-propane diol is a compound known per se, which is used, for example, in the preparation of polyesters and in the paint industry as one component of pulverous paints. The advantages of the compound include its very good UV shield and its very low adsorption of water.

The preparation of 2-n-butyl-2-ethyl-1,3-propane diol from 2-ethyl hexanal and formaldehyde by aldol addition, and so-called Cannizzaro reaction immediately following it, is per se known in organic chemistry. The said reactions are achieved by using in the reaction a basic alkali metal hydroxide or earth alkali metal hydroxide catalyst.

Japanese patent publication JP-48 043 085 describes a process for preparing 2-n-butyl-2-ethyl-1,3-propane diol from 2-ethyl hexanal and formaldehyde in the presence of a basic alkali metal hydroxide, in two steps, in the first of which a selective aldol condensation was allowed to occur at 30°–60 °C., the pH being 8–11. In the second step, a selective cross-Cannizzaro reaction was performed at 65°–90° C. at pH 8–11. However, the methods for the isolation and purification of the 2-n-butyl-2-ethyl-1,3-propane diol obtained as the final product are not reported, nor is the yield of final product.

JP patent publication 62 129 233 discloses a process for the preparation and purification of 2-n-butyl-2-ethyl-1,3-propane diol. In this process, the reaction mixture which is obtained as a result of a reaction of 2-ethyl hexanal and formaldehyde in the presence of an alkali metal hydroxide or an earth alkali metal hydroxide and water and which contains 2-n-butyl-2-ethyl-1,3-propane diol is neutralized with an organic acid or a mineral acid, the organic phase is separated, and one part of the organic phase is washed, once or several times, with 0.01–2 parts of water in order to remove the formaldehyde. Finally the organic phase is vacuum distilled. For this process, a final product yield of 91.9% is reported when the initial material used was paraformaldehyde.

In JP patent publication 2 062 836, the yield and grade of 2-n-butyl-2-ethyl-1,3-propane diol has been improved by adding to a mixture of 2-ethyl hexanal and formaldehyde in the presence of an alkali metal hydroxide in a heterogenous system 2% by weight or more (in proportion to the 2-ethyl hexanal) of $C_{14}$ alcohol. The phases are separated from a mixture neutralized with an organic acid or a mineral acid, and the pH of the organic phase is adjusted to 4.5–5.5 by means of phosphoric acid, before its vacuum distillation. In the example given, the reaction mixture contained 7.9% weight of methanol (in proportion to the 2-ethyl hexanal), the 2-n-butyl-2-ethyl-1,3-propane diol yield reported in this case being 94.4%.

In U.S. Pat. No. 2,413,803, 2-n-butyl-2-ethyl-1,3-propane diol is prepared from 2-ethyl hexanal and formaldehyde by means of potassium hydroxide from a homogenous mixture (homogenized with ethanol) in a multiple-step and long synthesis process, with a yield of 73%.

In U.S. Pat. No. 5,146,004, 2-ethyl-2-(hydroxymethyl)hexanal is prepared from 2-ethyl hexanal, formaldehyde and a tertiary amine. Any unreacted 2-ethyl hexanal can be isolated by azeotropic distillation of the organic phase of the raw product, and 2-butyl-2-ethyl-1,3 propane diol is obtained from the purified organic phase of the raw product by catalytic hydrogenation, with a yield of 85–88%. The hydrogenation is carried out by using a nickel catalyst.

In all of the processes according to the publications referred to above and in general in prior-art processes for the preparation of 2-n-butyl-2-ethyl-1,3-propane diol, multiple-step and even cumbersome reaction series are used. The yields reported are low, or they have not been reported at all, or according to experiments carried out in connection with the present invention the reported quite high yields cannot be achieved, with the exception of the test arrangement according to patent publication JP-2 062 836.

The object of the process according to the present invention is thus to prepare 2-n-butyl-2-ethyl-1,3-propane diol by a technically simple but efficient process which will result in a very high yield of the final product. It has been observed, surprisingly, that this object is achieved by selecting correctly the sources of the components participating in the reaction and by using a correctly selected catalyst combination. The process according to the invention for the preparation of 2-n-butyl-2-ethyl-1,3-propane diol from 2-ethyl hexanal and formaldehyde by using an alkali metal hydroxide catalyst or an earth alkali metal hydroxide catalyst is thus characterized in what is stated in the characterizing clause of Claim 1.

According to the present invention, 2-n-butyl-2-ethyl-1,3-propane diol according to Formula (I) is prepared from 2-ethyl hexanal (Formula II) and formaldehyde (Formula III)

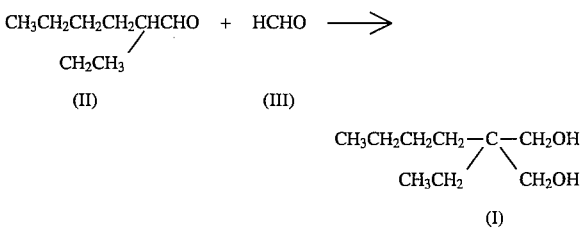

by using an alkali metal hydroxide or earth alkali metal hydroxide catalyst and, for promoting the efficiency of the reaction, a so-called cationic or neutral phase transfer catalyst. After the reaction step the mixture is neutralized with an organic acid or a mineral acid, the phases are separated, and the organic phase is washed with water and vacuum distilled.

With respect to catalysts, what is new and surprising in the process according to the present invention is specifically the use of the said catalysts, i.e. alkali metal hydroxide or earth alkali metal hydroxide catalysts + cationic or neutral phase transfer catalysts, in combination, for producing and promoting the desired reaction. Furthermore, it is essential in the invention that the formaldehyde source used is an almost methanol-free formalin solution which contains methanol less than 2%, or alternatively a solid paraformaldehyde.

In multiple-phase systems, which also the production process disclosed in the present invention is, inter-phase transfer of material is often a factor limiting the reaction velocity. The velocity and efficiency of the reaction can be increased by promoting inter-phase transfer of material by using so-called chemical phase transfer catalysts and/or by increasing the efficiency of the mechanical stirring, which, among other things, produces a considerably larger inter-phase contact surface. Chemical phase transfer catalysts are chemical compounds the property of which is to catalyze inter-phase transfer of material. Phase transfer catalysts may be cationic, anionic, or neutral.

In the process according to the present invention, the interesting phases are the organic phase and the aqueous phase. It has now been observed that in this case an advantageous end result, i.e. efficiency and speed of the reaction, is achieved by using a neutral or cationic phase-transfer catalyst together with an alkali metal hydroxide or earth alkali metal hydroxide. Polyethylene glycol can be mentioned as an example of neutral phase-transfer catalysts. Typical examples of cationic phase-transfer catalysts include tetrabutylammoniumhydrogen sulfate, $TBAHSO_4$, and tricaprylmethylammoniumhydrogen chloride.

The functioning principle of most cationic phase-transfer catalysts between an organic phase and an aqueous phase can be described as follows by using $TBAHSO_4$ as an example: In water, a large positive ion $TBA^+$ and a negative ion $HSO_4^-$.(alternatively $H^+$ and $SO_4^{-2}$) are released from a tetrabutylammoniumhydrogen sulfate molecule consisting of a pair of ions. When this positive ion comes into contact with a monovalent negative ion (e.g. $OH^-$), a new ion pair is formed the common structure of which is "fat". Owing to the formed "fat structure" this new ion pair passes easily and readily into the organic phase. When the ion pair is in the organic phase, its negative ion may react with a desired reactant. In this case, for example, NaOH reacts with 2-ethyl hexanal. Since the $OH^-$ brought by the ion pair reacts with an organic compound, the $TBA^+$ remains in the organic phase in ion form, which is disadvantageous. Thus the $TBA^+$ returns to the aqueous phase. In the aqueous phase it may again undergo the above procedure, taking the hydroxyl group into the organic phase.

By using polyethylene glycol as an example, the operating principle of a neutral phase transfer catalyst can, in turn, be described as follows: Polyethylene glycol, PEG, has no charge, and so its operating principle differs from that of the above-mentioned cationic phase transfer catalyst. PEG functions as a phase transfer catalyst by attaching to the positive ion and by forming a so-called crown ether structure. The free electrons of the oxygen atoms of the PEG attract the positive ions. The crown ether formed owing to the structure of the PEG passes into the organic phase. In order to maintain the electron equilibrium in the phase, also the negative ions pass into the organic phase. When, for example, sodium hydroxide is used, PEG forms with $Na^+$ a crown ether, which passes into the organic phase, and the $OH^-$ ions follow in order to maintain the electron equilibrium. Since the reaction taking place in the organic phase consumes hydroxyl ions, the above cycle repeats in order to maintain the electron equilibrium.

According to state-of-the-art technology, chemical phase transfer catalysts have not been used in the preparation of 2-n-butyl-2-ethyl-1,3-propane diol; their use together with basic catalysts, and additionally the use of correctly selected reaction components, in the production process according to the present invention constitute a new method for preparing the said compound in a manner advantageous and efficient in terms of process technology.

The chemical reactions taking place in the production process according to the invention can be described step by step with the following reaction formulae:

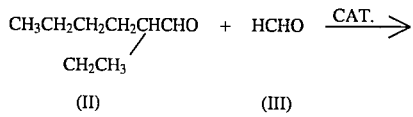

(II)    (III)

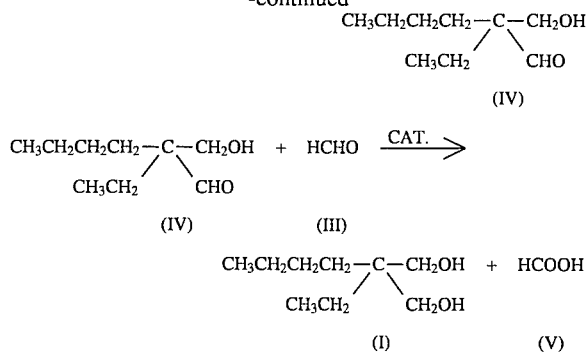

Thus, in the first reaction step 2-ethyl hexanal (Formula II) and formaldehyde (Formula III) react, forming an intermediate product β-hydroxyaldehyde according to Formula IV, i.e. 2-n-butyl-2-ethyl-3-hydroxide propanal. Since in terms of process economy it is most important that, immediately after this aldol reaction between the initial materials, there occurs the so-called Cannizzaro reaction, in which a portion of the formaldehyde (Formula III) is oxidized to the corresponding acid, i.e. formic acid (Formula V) and the intermediate product β-hydroxyaldehyde (Formula IV) is reduced to the corresponding alcohol, i.e. 2-n-butyl-2-ethyl-1,3-propane diol (Formula I), the catalyst used in the reaction must be either an earth alkali metal hydroxide or an alkali metal hydroxide.

The object of the present invention is thus that the intermediate product β-hydroxyaldehyde, i.e. 2-n-butyl-2-ethyl-3-hydroxy propanal, should form as rapidly and completely as possible, and that it should immediately be reduced as completely as possible to 2-n-butyl-2-ethyl-1,3-propane diol, and the formaldehyde used in excess in the reaction should be oxidized to formic acid, from which there is further formed an earth alkali metal salt or an alkali metal-salt, depending on the catalyst used. This object, i.e. maximally complete forming of β-hydroxyaldehyde and reduction to alcohol can now be achieved by selecting suitable reaction conditions and pure initial material components, which applies specifically to formaldehyde, and by additionally using, in accordance with the invention, neutral or cationic phase transfer catalysts. By means of these, the initially heterogenous reaction system is made more homogenous, the reaction is caused to occur more rapidly and to a more advanced degree, and the final result obtained is a surprisingly high yield of the desired 2-n-butyl-2-ethyl-1,3-propane diol.

It is also essential for an efficient and economical reaction that the source of the formaldehyde used as the initial material is selected correctly. This requirement is met when the formaldehyde source used is paraformaldehyde (more efficient use of the capacity) or an almost methanol-free (MeOH < 2% by weight) 30–53% by weight formalin solution. (The most economical alternative is to use, for example, a formalin solution coming directly from the process).

The molar ratio of the 2-ethyl hexanal to the formaldehyde, used as the initial materials of the reaction, should be within the range 1:2 to 1:4, preferably within the range 1:2.5 to 1:3.5. To the mixture is added a neutral or cationic phase transfer catalyst, such as neutral polyethylene glycol (e.g. PEG 400) or a cationic tetrabutylammoniumhydrogen sulfate ($TBAHSO_4$) or tricaprylmethylammonium chloride (Aliquat 336). These are added in an amount of 1–50% by weight, preferably 5–30% by weight, of the mass of the formalin solution or, if solid paraformaldehyde is used, in an amount of 1–20% by weight, preferably 3–10% by weight, of the mass of the aqueous solution and solid paraformaidehyde, or in an amount of 1–50% by weight, preferably 5–15% by weight, of the amount of 2-ethyl hexanal. The mixture of the initial materials is heated to 30°–100° C., preferably to 50°–80° C., and most preferably to 60°–80° C., and an aqueous solution of the alkali metal hydroxide or earth alkali metal hydroxide is added to the mixture, drop by drop, in the course of up to 5 h, preferably 1–3 h, and the reaction is continued at the said temperature for up to 3 h, preferably 15 min–2 h, most preferably 15 min–1 h 15 min. The alkali metal hydroxide or earth alkali metal hydroxide is used in a molar amount 1:1 to 2:1, preferably in a molar amount of 1.25:1 to 1.75:1 to that of 2:1-ethyl hexanal. After this reaction step the mixture is neutralized with an organic acid or a mineral acid, preferably for example sulfuric acid, and the phases are separated from each other, preferably while they are hot. The organic phase is washed with water once or several times, preferably 1–2 times, by using for the wash an amount of water at minimum 50% of the mass of the organic phase. The phases are separated and the organic phases are combined and vacuum distilled. The boiling point of the final product is 130°–132° C./9 mmHg. The yield obtained for 2-n-butyl-2-ethyl-1,3-propane diol was up to more than 92%, depending on the reaction conditions and the molar proportions.

The preferred embodiments achieved using the cationic or neutral phase transfer catalysts used in the process according to the invention are determined according to the formaldehyde source used. If the formaldehyde source used is a formalin solution which contains methanol less than 2%, preferably less than 1%, both cationic and neutral phase transfer catalysts are suitable as phase transfer catalysts for achieving an advantageous end result. If solid paraformaldehyde is used as the source of formaldehyde, it is most preferable to use a cationic phase transfer catalyst, such as the above-mentioned tetrabutylammoniumhydrogen sulfate or tricaprylmethylammonium chloride, to achieve as high a yield as possible.

The process according to the invention described above for the preparation of 2-n-butyl-2-ethyl-1,3-propane diol is a simple, reliable, efficient, and high-yield method of preparing the said compound.

The production process according to the invention is illustrated in greater detail in the following examples. However, they are intended only to illustrate the invention and must not be understood as limiting the invention.

Examples in which a formalin solution was used as the source of formaldehyde:

EXAMPLE 1

136.3 g of a 45% formalin solution which contained less than 1% of methanol, 100.5 g of 2-ethyl hexanal, and 13.8 g (10% by weight of the mass of the formalin solution) of a neutral phase transfer catalyst, i.e. polyethylene glycol (PEG 400) were placed in a reactor, and the mixture was heated to 70° C. 142.0 g of an aqueous solution of NaOH was added to the mixture in the course of 2 h, and the reaction was continued for 45 minutes. The mixture was neutralized with sulfuric acid, the phases were separated, and the organic phase was washed twice with water. The final product was vacuum distilled at 130°–132° C./9 mmHg, whereby 116.5 g of 2-n-butyl-2-ethyl-1,3-propane diol distilled out, corresponding to a yield of 92.7% calculated from the 2-ethyl hexanal.

EXAMPLE 2

The reaction was performed in a manner corresponding to that in Example 1, but polyethylene glycol was used in an amount of 30% by weight of the mass of the formalin solution. 2-n-butyl-2-ethyl-1,3-propane diol distilled out with a yield of 94.2%.

EXAMPLE 3

The reaction was performed in a manner corresponding to that in Example 1, but polyethylene glycol was used in an amount of only 3% by weight of the mass of the formalin solution. 2-n-butyl-2-ethyl-1,3-propane diol distilled out with a yield of 84.1%.

EXAMPLE 4

The reaction was performed in a manner corresponding to that in Example 1, but polyethylene glycol was used in an amount of only 1% by weight of the mass of the formalin solution. 2-n-butyl-2-ethyl-1,3-propane diol distilled out with a yield of 76.7%.

EXAMPLE 5

69.8 g of a 45% formalin solution which contained less than 1% by weight of methanol, 50.2 g of 2-ethyl hexanal, and 4.1 g (5.9% by weight of the mass of the formalin) of a cationic phase transfer catalyst, Aliquat 336, were heated to 60° C., and 71.0 g of an aqueous solution of NaOH was added to the solution in the course of 2 h. The mixture was heated for 45 minutes, whereafter it was neutralized with sulfuric acid. The phases were separated, and the organic phase was washed once with water. 55.7 g of 2-n-butyl-2-ethyl-1,3-propane diol distilled out at 130°–132° C./9 mmHg; this corresponds to a yield of 88.8%.

EXAMPLE 6

The reaction was performed as in Example 5, but Aliquat 336 was replaced with tetrabutylammoniumhydrogen sulfate, $TBAHSO_4$, which was used in an amount of 6.0% by weight of the mass of the formalin solution. 2-n-butyl-2-ethyl-1,3-propane diol distilled out with a yield of 84.6%.

EXAMPLE 7

134.0 g of a 45% formalin solution which contained methanol less than 1% by weight, 100.6 g of 2-ethyl hexanal, and 13.3 g (10% by weight of the mass of the formalin) of a cationic phase transfer catalyst, Aliquat 336, were heated to 70° C., and 142 g of an aqueous solution of NaOH was added to the mixture in the course of 2 h 20 min. The mixture was stirred for 45 minutes, whereafter it was neutralized with sulfuric acid. The phases were separated, and the organic phase was washed once with water. 117.0 g of 2-n-butyl-2-ethyl-1,3-propane diol distilled out at 130°–132° C./9 mmHg; this corresponds to a yield of 93.0%.

EXAMPLE 8

The reaction was performed as in Example 7, but Aliquat 336 was replaced with tetrabutylammoniumhydrogen sulfate, $TBAHSO_4$, which was used in an amount of 10% by weight of the mass of the formalin solution. 2-n-butyl-2-ethyl-1,3-propane diol distilled out with a yield of 87.8%.

EXAMPLE 9, COMPARATIVE EXAMPLE

The reaction was carried out in a manner corresponding to that of Example 1, but no phase transfer catalyst was used in the reaction. 2-n-butyl-2-ethyl-1,3-propane diol distilled out with a yield of 76.5%.

Examples in which the source of formaldehyde is solid paraformaidehyde:

EXAMPLE 10

29.9 g of solid paraformaldehyde, 50 g of water, 50.0 g of 2-ethyl hexanal, and 4.1 g of a cationic phase transfer catalyst, Aliquat 336, (5.1% by weight of the mass of the aqueous solution of paraformaldehyde) were heated to 60° C., and 125.0 g of an aqueous solution of NaOH was added to the mixture in the course of 1.5 hours. The mixture was further stirred for 1.5 h and was then neutralized with sulfuric acid. The phases were separated, and the organic phase was washed twice with water. 56.9 g of 2-n-butyl-2-ethyl-1,3-propane diol distilled out at 130°–132 ° C./9 mmHg, with a yield of 91.0%.

EXAMPLE 11

29.9 g of solid paraformaldehyde, 50 g of water, 50.2 g of 2-ethyl hexanal, and 4.1 g of a cationic phase transfer catalyst, TBAHSO$_4$, (5.2% by weight of the mass of the aqueous solution of paraformaldehyde) were heated to 60° C., and 125.0 g of an aqueous solution of NaOH was added to the mixture in the course of 2 h. The mixture was further stirred for 1 h and was neutralized with sulfuric acid. The phases were separated, and the organic phase was washed twice with water. 55.0 g of 2-n-butyl-2-ethyl-1,3-propane diol distilled out, with a yield of 87.7%.

EXAMPLE 12

The reaction was performed as in Example 11 but, instead if a cationic phase transfer catalyst, a neutral phase transfer catalyst, polyethylene glycol, was used in an amount of 4.0 g (4.9% by weight of the mass of the aqueous solution of paraformaldehyde). The obtained yield of 2-n-butyl-2-ethyl-1,3-propane diol was only 73.2%.

EXAMPLE 13, COMPARATIVE EXAMPLE

The reaction was performed as in Example 9, but no phase transfer catalyst was used. The obtained yield of 2-n-butyl-2-ethyl-1,3-propane diol was only 73.2%.

The above examples show clearly that, when cationic or neutral phase transfer catalysts are used, a significantly better yield is obtained than without these catalysts. Furthermore, it can be noted that in the preferred embodiments it is possible to use both cationic and neutral phase transfer catalysts if the formaldehyde source is an almost methanol-free formalin solution, but if solid paraformaldehyde is used it is preferable to use a cationic phase transfer catalyst.

We claim:

1. A process for the preparation of 2-butyl-2-ethyl-1,3-propane diol, which comprises:

reacting 2-ethyl hexanal and formaldehyde in the presence of a basic alkali metal hydroxide or earth alkali metal hydroxide catalyst, wherein the formaldehyde source is solid paraformaldehyde, and a cationic phase transfer catalyst is used for promoting the reaction.

2. A process according to claim 1, wherein said cationic phase transfer catalyst is tricaprylmethylammonium chloride or tetrabutylammoniumhydrogen sulfate.

\* \* \* \* \*